(12) United States Patent
Lim

(10) Patent No.: US 8,783,097 B2
(45) Date of Patent: Jul. 22, 2014

(54) SYSTEM FOR SENSING SOOT OF DIESEL VEHICLE

(71) Applicant: Hyundai Motor Company, Seoul (KR)

(72) Inventor: Cheol Beom Lim, Whasung-Si (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 13/683,759

(22) Filed: Nov. 21, 2012

(65) Prior Publication Data
US 2014/0000354 A1    Jan. 2, 2014

(30) Foreign Application Priority Data
Jun. 29, 2012    (KR) .......................... 10-2012-0071125

(51) Int. Cl.
*G01M 15/10* (2006.01)

(52) U.S. Cl.
USPC ..................... 73/114.75; 73/23.33; 73/114.71

(58) Field of Classification Search
CPC . F01N 2560/05; F01N 11/00; F01N 2560/20; F01N 11/007; G01N 1/2252; G01N 25/00
USPC ..................... 73/23.31, 23.33, 114.71, 114.75
See application file for complete search history.

(56) References Cited

U.S. PATENT DOCUMENTS

| 4,322,383 | A |   | 3/1982  | Yasuda et al. |   |
|---|---|---|---|---|---|
| 5,549,871 | A |   | 8/1996  | Kocache et al. |   |
| 5,753,188 | A |   | 5/1998  | Shimoda et al. |   |
| 7,977,955 | B2 | * | 7/2011  | Katsuyama et al. | 324/693 |
| 8,033,159 | B2 | * | 10/2011 | Fleischer et al. | 73/28.01 |
| 8,191,353 | B2 | * | 6/2012  | Kakinohana et al. | 60/275 |
| 8,490,465 | B2 | * | 7/2013  | Ante et al. | 73/23.2 |
| 8,561,388 | B2 | * | 10/2013 | Yahata et al. | 60/277 |
| 2010/0126248 | A1 | * | 5/2010 | Hall | 73/23.33 |
| 2011/0015824 | A1 | * | 1/2011 | Ante et al. | 701/34 |
| 2012/0103059 | A1 | * | 5/2012 | Kimata et al. | 73/23.33 |
| 2012/0144813 | A1 | * | 6/2012 | Yahata et al. | 60/311 |
| 2013/0189802 | A1 | * | 7/2013 | Tromp et al. | 438/14 |

FOREIGN PATENT DOCUMENTS

JP    2000-18024 A    1/2000

OTHER PUBLICATIONS

Lim et al., "Preliminary study on catalytic combustion-type sensor for the detection of diesel particulate matter," Sensors and Actuators B 160 (2011) pp. 463-470.
Cheol-Beom Lim, *Response of Catalytic Combustion-type Sensor to Different Amounts of Diesel Particulate Matter*, Journal of Novel Carbon Resource Sciences, Sep. 2011, pp. 1-7, vol. 4, Kyushu University Global COE Program.
Cheol-Beom Lim, *Catalytic performance of supported precious metal catalysts for the combustion of diesel particulate matter*, Catalysis Today 175, 2011, pp. 106-111.

* cited by examiner

*Primary Examiner* — Freddie Kirkland, III
(74) *Attorney, Agent, or Firm* — Morgan, Lewis & Bockius LLP

(57) ABSTRACT

A system for sensing soot of a diesel engine includes a combustion element which is a porous ceramic structure and to which a catalytic substance that is combustion-reacted with the soot is fixed, a comparison element which is the porous ceramic structure and to which a stable substance that is not combustion-reacted with the soot, and a detection section for detecting the temperatures of the combustion element and the comparison element and for deducing the soot formation amount among exhaust gas by using the temperature difference of the respective element.

8 Claims, 1 Drawing Sheet

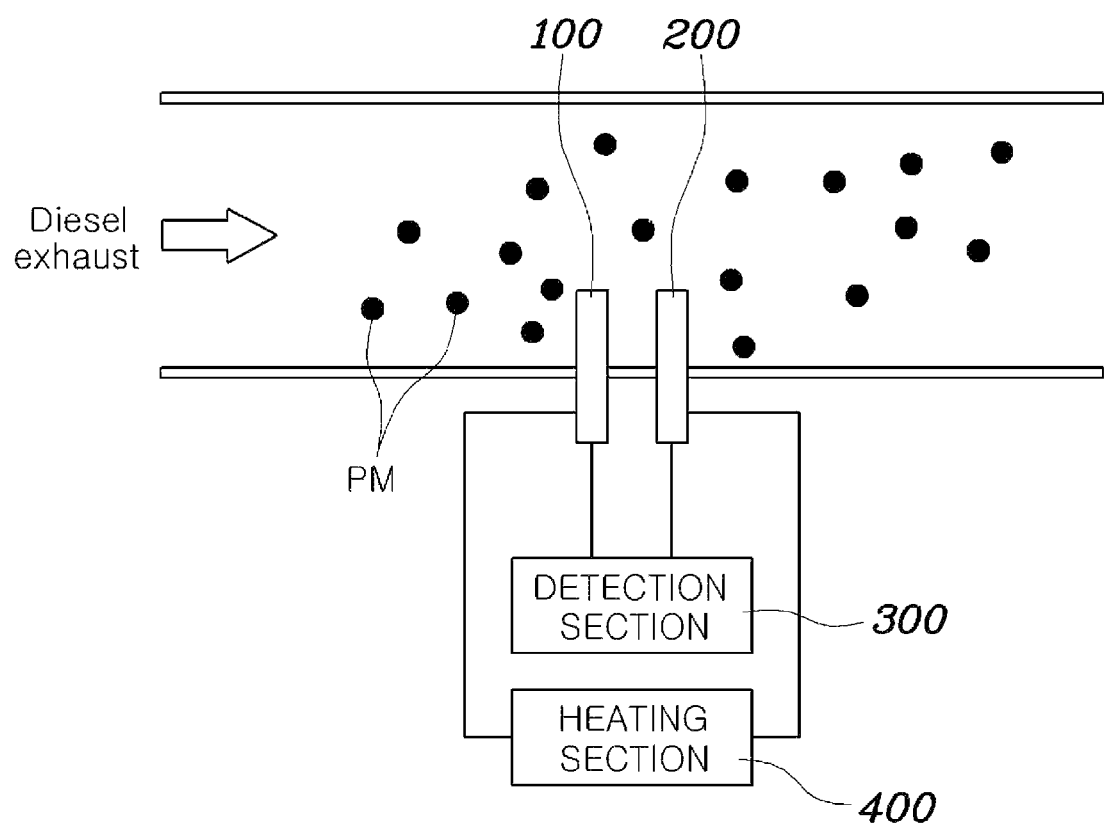

SYSTEM FOR SENSING SOOT OF DIESEL VEHICLE

CROSS-REFERENCE TO RELATED APPLICATION

The present application claims priority of Korean Patent Application Number 10-2012-0071125 filed Jun. 29, 2012, the entire contents of which application is incorporated herein for all purposes by this reference.

BACKGROUND OF INVENTION

1. Field of Invention

The present disclosure relates to a system for deducing the soot formation amount discharged from a diesel engine.

2. Description of Related Art

Generally, in a Diesel Particulate Filter ("DPF") system the Particulate Matters ("PM") remaining in a exhaust gas of a diesel engine are collected physically by using a filter and then PM is burnt out by increasing a temperature of the exhaust gas to an combustion temperature of PM or more after a vehicle travels at a predetermined distance.

The DPF system has been kwon as the best efficient technology for removing the soot among PM, however, an additional back pressure has to be applied to an engine and further the additional energy consumption is necessary for burning and reproducing periodically the traped-soot since the exhaust gas temperature has to be increased under the DPF system thereby affecting adversely fuel efficiency. Further, the discharged soot is affected greatly by an engine operation condition.

Accordingly, there needs a technology for sensing discharging amount of soot in real time in order to operate efficiently an engine and optimize DPF operation period.

Meanwhile, according to a related art, an optical sensor has been mainly used for sensing the soot and recently a Radio Frequency ("RF") based sensor has been proposed, however, the RF based sensor is impossible to sense in real time selectively the soot and further costs high and has large volume and thus it has limitation to being mounted practically on a vehicle.

Accordingly, a development of a contact combustion type diesel soot sensor of a new concept that is applicable to a vehicle is necessary and further a development of a catalyst having selectively high combustion activity with respect to the soot is essential for implementing the contact combustion type soot sensor.

The information disclosed in this Background section is only for enhancement of understanding of the general background of the invention and should not be taken as an acknowledgement or any form of suggestion that this information forms the prior art already known to a person skilled in the art.

SUMMARY OF INVENTION

Various aspects of the present invention provide for a system for sensing selectively in real time soot formation amount among PM in exhaust gas of a diesel engine.

Various aspects of the present invention provide for a system for sensing soot of a diesel engine, including a combustion element which is a porous ceramic structure and to which a catalytic substance that is combustion-reacted with the soot is fixed, a comparison element which is the porous ceramic structure and to which a stable substance that is not combustion-reacted with the soot is fixed, and a detection section for detecting the temperatures of the combustion element and the comparison element and for deducing the soot formation amount among exhaust gas by using the temperature difference of the respective element.

The ceramic structure may include Al2O3.
The ceramic structure may include SiO2.
The stable substance may consist mainly of TiO2.
The catalytic substance may use TiO2 as a support and consists of a fixed element that is combustion-reacted with the soot.

The system for sensing soot of a diesel engine may further include a heating section for heating the combustion element so that the catalytic substance is combustion-reacted with the soot among exhaust gas.

The heating section may heat equally the combustion element and the comparison element.

The detection section may deduce the soot formation amount among exhaust gas by converting the temperature difference produced between the combustion element and the comparison element into electric signal.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 1 is a view showing an exemplary system for sensing soot of a diesel engine according to the present invention.

It should be understood that the appended drawings are not necessarily to scale, presenting a somewhat simplified representation of various features illustrative of the basic principles of the invention.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

FIG. 1 is a view showing a system for sensing soot of a diesel engine according to various embodiments of the present invention, referring to FIG. 1, the system for sensing soot of a diesel engine includes a combustion element 100 which is porous ceramic structure and to which a catalytic substance that is combustion-reacted with soot in exhaust gas of a diesel engine is fixed, a comparison element 200 which is porous ceramic structure and to which a catalytic substance that is stable and combustion-inactive with soot in exhaust gas of a diesel engine is fixed, and a detection section 300 for detecting the temperature difference between the combustion element 100 and the comparison element 200 and deducing the soot formation amount among the soot in exhaust gas by using the temperature difference of the respective element.

That is, the present invention relates to a system for sensing soot by using the catalyst that is positively and high active with respect to the soot and for deducing positively the soot discharging amount among PM in exhaust gas discharged from a diesel engine.

Specially, the system for sensing the soot is configured by the combustion element 100 to which the catalytic substance that is high combustion-active with respect to the soot is fixed and the comparison element 200 that is stable and combustion-inactive with respect to the soot wherein when the combustion element 100 is heat-reacted with the soot and thus temperature increases, the temperature difference between the combustion element and the comparison element 200 is detected through the detection section to deduce the soot discharging amount.

Here, the combustion element 100 may consist of Ag as the catalytic substance that is selectively combustion-reacted with the soot and the catalytic substance is fixed to the porous ceramic structure. Meanwhile, the comparison element 200 is a comparison means for measuring the combustion heat amount produced when the combustion element 200 is combustion-reacted with the soot and further may consist mainly of $TiO_2$ that is not combustion-reacted with the soot.

Accordingly, the temperature variation and the temperature difference between the combustion element 100 which consists of the catalytic substance that is positively combustion-reacted with the soot and the comparison element 200 which consists of stable substance that is not combustion-reacted with the soot are measured through the detection section 300 to deduce the soot formation amount and then convert it into electrical signal thereby sensing the soot formation amount in real time.

Meanwhile, the ceramic structure constituting the combustion element 100 and the comparison element 200 may comprise $Al_2O_3$ or $SiO_2$ as a porous structure.

Of course, the ceramic structure may comprise other materials, however, it may comprise $Al_2O_3$ or $SiO_2$, since $Al_2O_3$ or $SiO_2$ is stable as the structure and is not catalytic-active with respect to the soot and is not reacted with other materials. Further, the ceramic structure may be porous such that the catalytic substance and other materials are fixed thereto.

Meanwhile, the stable substance that is fixed to the comparison element 200 may consist mainly of $TiO_2$. The present invention intends to deduce the soot formation amount by using the temperature difference between the combustion element 100 that is selectively combustion-reacted with the soot in exhaust gas of a diesel engine and the comparison element 200 that is not combustion-reacted with the soot wherein the substance that is not combustion-reacted with the soot has to be used in the comparison element. Accordingly, $TiO_2$ as the stable substance that is not combustion-reacted with the soot is comprised in the comparison element. Further, the more $TiO_2$ which is fixed to the ceramic structure is comprised, the more the effect as the stable substance increases and pure $TiO_2$ may be very suitable.

Meanwhile, the catalytic substance may use $TiO_2$ as a support and Ag that is combustion-reacted with the soot may be fixed thereto, that is because that the support of the catalytic substance that is fixed to the combustion element 100 and the stable substance that is fixed to the comparison element 200 consist of $TiO_2$ and thus the combustion heat amount produced through the combustion reaction with the soot can be quantified. Further, in case of Ag used in the catalytic substance, since Ag has selectively and high catalytic activity with respect to the soot, Ag may be utilized as an element that is fixed to the catalytic substance of the combustion element.

As a result, the temperature difference between the combustion element 100 and the comparison element 200 is produced to deduce the soot discharging amount and, the support of the catalytic substance that is fixed to the combustion element 100 and the stable substance that is fixed to the comparison element 200 consist of $TiO_2$ and thus the temperature difference caused from the combustion reaction can be measured accurately.

Meanwhile, the present invention further includes a heater section 400 for heating the combustion element 100 such that the catalytic substance is to be combustion-reacted with the soot in exhaust gas. Generally, the exhaust gas temperature of a diesel engine is not enough burn the soot and thus the heater section heats the combustion element 100 to a predetermined temperature so that the catalytic substance is combustion-reacted with the soot.

As a result, the combustion element 100 is catalytic combustion-reacted with the soot and thus the soot formation amount among the exhaust gas can be deduced by using the temperature difference between the combustion element 100 of increased temperature the comparison element 200.

Specially, the heater section 400 may heat equally the combustion element 100 and the comparison element 200 that is because that in addition to the temperature difference caused from the combustion reaction of the combustion element 100 with the soot, when the temperature difference is caused from heating only the combustion element 100 or other conditions, the accurate deducing of the soot formation amount of the combustion element 100 and the comparison element 200 is limited. Accordingly, the heater section 400 may heat equally the combustion element 100 and the comparison element 200 in order to quantify the temperatures of the combustion element 100 and the comparison element 200.

Meanwhile, the detection section 300 may deduce the soot formation amount in exhaust gas by converting the temperature difference produced between the combustion element 100 and the comparison element 200 into electric signal.

In more detailed description, the temperature difference between the combustion element 100 and the comparison element 200 can be deduced by using a contact combustion type sensor. When the combustion element 100 contacts the soot among exhaust gas and is combustion-reacted to increase temperature thereby increasing electric resistance. At this time, the electric resistance variation is converted into electric signal and the soot formation amount can be deduced by comparing the electric signal to the electric signal of the comparison element 200. As a result, the soot formation amount cab be confirmed in real time and prompt management thereto can be made.

According to the system for sensing the soot of a diesel engine, the soot formation amount can be deduced and sensed in real time by applying the catalytic substance having high combustion-activity with respect to the soot among PM in exhaust gas discharged from a diesel engine to the combustion element.

Specially, according to the system for sensing the soot of a diesel engine, the soot formation amount can be sensed by using the temperature difference between the combustion element consisting of the catalytic substance that is high combustion-active with respect to the soot and the comparison element that is not combustion-inactive with respect to the soot.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A system for sensing soot of a diesel engine, comprising: a combustion element including a porous ceramic structure to which a catalytic substance that combustion-reacts with the soot is fixed; a comparison element including the porous ceramic structure to which a stable substance that does not combustion-react with the soot is fixed; and a detection section for detecting the temperatures of the combustion element and the comparison element and for deducing the soot formation amount among exhaust gas by using the temperature difference of the respective element.

2. The system for sensing soot of a diesel engine of claim 1, wherein the ceramic structure comprises Al2O3.

3. The system for sensing soot of a diesel engine of claim 1, wherein the ceramic structure comprises SiO2.

4. The system for sensing soot of a diesel engine of claim 1, wherein the stable substance consists mainly of TiO2.

5. The system for sensing soot of a diesel engine of claim 1, wherein the catalytic substance uses TiO2 as a support and consists of a fixed element that is combustion-reacted with the soot.

6. The system for sensing soot of a diesel engine of claim 1, further comprising a heating section for heating the combustion element so that the catalytic substance is combustion-reacted with the soot among exhaust gas.

7. The system for sensing soot of a diesel engine of claim 6, wherein the heating section heats equally the combustion element and the comparison element.

8. The system for sensing soot of a diesel engine of claim 1, wherein the detection section deduces the soot formation amount among exhaust gas by converting the temperature difference produced between the combustion element and the comparison element into electric signal.

* * * * *